United States Patent [19]

Prager et al.

[11] Patent Number: 5,580,978
[45] Date of Patent: Dec. 3, 1996

[54] PROCESS FOR THE PRODUCTION OF 7-ACA DERIVATIVES

[75] Inventors: Bernhard C. Prager, Wörgl; Hubert Sturm, Innsbruck, both of Austria

[73] Assignee: Biochemie Gesellschaft m.b.H., Austria

[21] Appl. No.: 421,099

[22] Filed: Apr. 13, 1995

Related U.S. Application Data

[63] Continuation of Ser. No. 139,479, Oct. 20, 1993, abandoned, which is a continuation of Ser. No. 917,570, Jul. 20, 1992, abandoned, which is a continuation of Ser. No. 731,696, Jul. 17, 1991, abandoned, which is a continuation of Ser. No. 515,292, Apr. 27, 1990, abandoned, which is a continuation of Ser. No. 427,656, Oct. 26, 1989, abandoned, which is a continuation of Ser. No. 369,431, Jun. 21, 1989, abandoned, which is a continuation of Ser. No. 307,030, Feb. 3, 1989, abandoned, which is a continuation of Ser. No. 870,258, Jun. 3, 1986, abandoned.

[30] Foreign Application Priority Data

Jun. 3, 1985 [AT] Austria ................................. 1669/85

[51] Int. Cl.⁶ .................................................. C07D 501/18
[52] U.S. Cl. .............................................................. 540/230
[58] Field of Search ..................................... 540/222, 230

[56] References Cited

U.S. PATENT DOCUMENTS

| | | | |
|---|---|---|---|
| 3,665,003 | 5/1972 | Kennedy et al. | 540/230 |
| 4,317,907 | 3/1982 | Saikawa et al. | 540/221 |
| 4,482,710 | 11/1984 | Fujimoto et al. | 540/220 |
| 4,902,793 | 2/1990 | Nishikido et al. | 540/230 |

*Primary Examiner*—John M. Ford
*Attorney, Agent, or Firm*—Robert S. Honor; Melvyn M. Kassenoff; Thomas O. McGovern

[57] ABSTRACT

The invention provides an improved process for the production of 7-amino-3-alkoxymethlycephem-4-carboxyl acid derivatives.

10 Claims, No Drawings

PROCESS FOR THE PRODUCTION OF 7-ACA DERIVATIVES

This is a continuation of application Ser. No. 08/139,479, filed Oct. 20, 1993, now abandoned, which in turn is a continuation of application Ser. No. 07/917,570, filed Jul. 20,1992, now abandoned, which in turn is a continuation of application Ser. No. 07/731,696, filed Jul. 17, 1991, now abandoned, which in turn is a continuation of application Ser. No. 07/515,292, filed Apr. 27, 1990, now abandoned, which in turn is a continuation of application Ser. No. 07/427,656, filed Oct. 26, 1989, now abandoned, which in turn is a continuation of application Ser. No. 07/369,431, filed Jun. 21, 1989, now abandoned, which in turn is a continuation of application Ser. No. 07/307,030, filed Feb. 3, 1989 now abandoned, which in turn is a continuation of application Ser. No. 06/870,258, filed Jun. 3, 1986, now abandoned.

This invention relates to a new process for the production of 7-amino-3-alkoxymethyl-3-cephem-4-carboxylic acid derivatives of formula I,

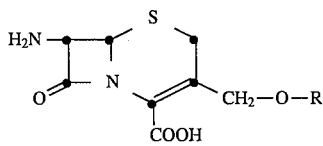

in which R signifies lower alkyl.

Processes for the production of these compounds are known but have certain disadvantages, for example moderate yields only. Thus, for example, processes involving reaction of 7-aminocephalosporanic acid (7-ACA) with lower alkanols in the presence or absence of catalysts are well known from for example Belgian patent 719,710, Japanese patent applications 57/192 392 and 59/103 387 and UK Patent application 2,110,688 but tend to give low yields. Other known processes proceed over 7-substituted (usually acylated) 7-ACA derivatives but these processes require higher technical effort and raw material requirements [basically requiring 3-steps-7-substitution (acylation) of 7-ACA, introduction of the 3-alkoxy-methyl substituent and removal of the 7-substituent (deacylation)] and are often also accompanied by low overall yields [see, for example Japanese patent applications 59/163 388 and 57/192 392 and J. Med. Chem. 14(2), 113 (1971)].

The present invention provides a novel process for the production of the compounds of formula I comprising reacting 7-ACA of formula II,

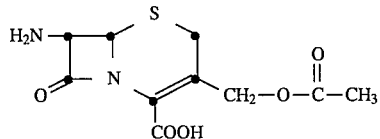

with a compound of formula III,

   III in which R is as defined above,
in the presence of boron trifluoride ($BF_3$) or a complex thereof.

The process of the invention is suitably effected in an organic solvent, for example an organic nitrile such as acetonitrile or propionitrile, a nitroalkane, such as nitromethane, or a sulphone, such as sulfolan. Preferred lower alkanols of formula III have 1 to 6, more preferably 1 to 4 carbon atoms, and include methanol, ethanol, n-propanol, isopropanol and n-butanol. The reaction is suitably carried out using the alcohol in equimolar amounts or in slight excess in relation to the boron trifluoride. The boron trifluoride may be used as such or in the form of well-known complexes, for example as described in DOS 2,804,896. A preferred complex is however a complex of $BF_3$ with the alcohol of formula III being employed. The $BF_3$ and the alcohol are suitably used in molar excess in relation to the compound of formula II, for example a 2 to 15-fold molar excess. The process is suitably carried out at a temperature of from 0° to 70°, preferably from room temperature to 50° C.

The resulting compounds of formula I may be isolated and purified using conventional techniques.

The process of the invention leads to the products of formula I in high yield (for example in yields of over 60%) and brings therefore substantial economies particularly as it operates in simple manner with relatively inexpensive chemicals. Furthermore, in contrast to certain known processes, the formation of undesired by-products, for example 7-ACA lactone, can be largely avoided and the product of formula I can therefore be isolated more simply since fewer by-products need to be removed.

The compounds of formula I are known starting materials for the production of valuable known cephalosporin antibiotics.

The following example, in which temperatures are in degrees Centigrade, illustrates the invention.

EXAMPLE (6R, 7R)-7-Amino-3-methoxymethyl-3-cephem-4-carboxylic acid 24 g of boron trifluoride gas is introduced under an insert atmosphere in to 60 g of sulfolan containing 10% methanol 6.5 ml of methanol are added and the temperature set at 50° 10.88 g of 7-aminocephalosporanic acid are added to the reaction mixture which is then stirred for 75 minutes at 50°. The mixture is diluted with cold methanol and the pH adjusted to 3.5 by addition of triethylamine. The precipitated mixture is stirred for a further 1 hour at 0° and the precipitate is filtered off, washed with methanol and dried to obtain the heading compound, having the following NMR data (which corresponds to published NMR data for this product)

$^1$H-NMR (90 MHz; $D_2O$, DCl): 5.39 (d, 1H, $H_7$, J=5 Hz); 5.31 (d, 1H, $H_6$, J=5 Hz). 4.46 (s, 2H, C—$CH_2$—O); 3.73 (2H, $H_2$ and $H_2$); 3.42 (s, 3H, O—$CH_3$).

What is claimed is:

1. A process for the production of a compound of formula I,

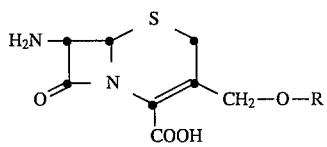

in which R signifies lower alkyl, which comprises reacting a compound of formula II,

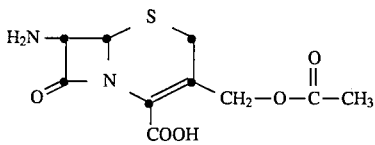

with a compound of formula III,

 III in which R is as defined above,
in the presence of boron trifluoride or a complex form thereof.

2. A process according to claim 1, in which the reaction is effected in an organic solvent selected from a nitrile, a nitroalkane and a sulphone.

3. A process according to claim 1 in which the compound of Formula III is methanol, ethanol, n-propanol, isopropanol, or n-butanol.

4. A process according to claim 1 in which the boron trifluoride complex form is a complex of boron trifluoride with a compound of Formula III.

5. A process for the production of a compound of formula I,

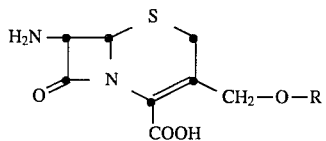

in which R signifies methyl,
which comprises reacting a compound of Formula II,

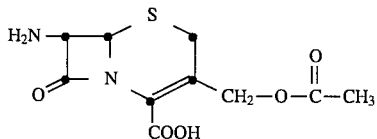

with methyl alcohol in the presence of boron trifluoride or a boron trifluoride complex with methyl alcohol, wherein an equimolar amount or slight excess of methyl alcohol is used in relation to the boron trifluoride.

6. A process according to claim 5, in which the reaction is carried out in an organic solvent selected from acetonitrile, propionitrile, nitromethane, and sulfolane.

7. A process according to claim 5, in which the reaction is carried out at a temperature between 0° and 70° C.

8. A process according to claim 5, in which the reaction is carried out between room temperature and 50° C.

9. A process for the production of (6R,7R)-7-amino-3-methoxymethyl-3-cephem-4-carboxylic acid according to claim 5, which comprises reacting 7-aminocephalosporanic acid with methanol in the presence of a boron trifluoride complex formed by boron trifluoride gas and methanol.

10. A process for the production of a cephalosporin antibiotic which comprises:

a) reacting a compound of Formula II,

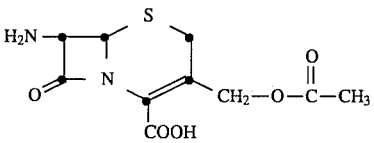

with a compound of formula III

 III where R is lower alkyl, in the presence of boron trifluoride or a boron trifluoride complex to obtain a compound of formula I

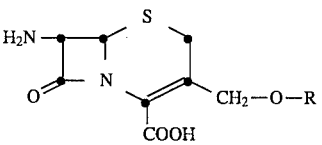

and b) acylating the compound of formula I with the 7-amino substituent of the cephalosporin antibiotic.

* * * * *